United States Patent [19]

Zink et al.

[11] 4,372,886
[45] Feb. 8, 1983

[54] PROCESS FOR THE PRODUCTION OF CARBINOL BASES FROM INDOLINE COMPOUNDS

[75] Inventors: Rudolf Zink, Therwill; Peter Loew, Münchenstein, both of Switzerland

[73] Assignee: Ciba-Geigy Corporation, Ardsley, N.Y.

[21] Appl. No.: 268,956

[22] Filed: Jun. 1, 1981

[30] Foreign Application Priority Data

Jun. 11, 1980 [CH] Switzerland ............... 4491/80

[51] Int. Cl.³ ............ C09B 55/00; C07D 211/72; C07D 211/73
[52] U.S. Cl. ............ 260/165; 542/417; 542/419
[58] Field of Search .......... 542/417, 419; 260/165

[56] References Cited

U.S. PATENT DOCUMENTS

| | | | |
|---|---|---|---|
| 3,345,355 | 10/1967 | Raue | 542/417 |
| 3,346,322 | 10/1967 | Finkenauer et al. | 8/79 |
| 3,769,279 | 10/1973 | Kuhlthau et al. | 542/417 |
| 3,773,764 | 11/1973 | Lehment et al. | 542/417 |
| 3,973,903 | 8/1976 | Clarke | 542/417 |
| 3,992,140 | 11/1976 | Psaar | 8/2.5 A |
| 4,026,885 | 5/1977 | Frey et al. | 260/240 G |
| 4,251,656 | 2/1981 | Leow et al. | 542/417 |
| 4,281,112 | 7/1981 | Lehment et al. | 542/419 |

FOREIGN PATENT DOCUMENTS 1544290 4/1979 United Kingdom .

*Primary Examiner*—Arthur P. Demers
*Attorney, Agent, or Firm*—Edward McC. Roberts

[57] ABSTRACT

The invention describes a novel single step process for the production of carbinol bases of the formula I

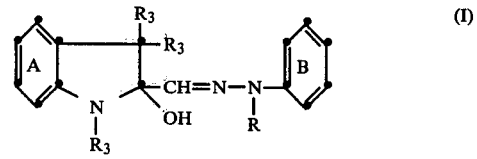

wherein R is the methyl or ethyl group, each $R_3$ independently is a $C_1$–$C_4$ alkyl group and the benzene rings A and/or B can be unsubstituted or substituted, which process comprises alkylating 1 mole of a dye base of the formula II

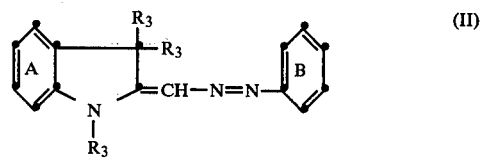

or the hydrogen salt thereof of the formula IIa

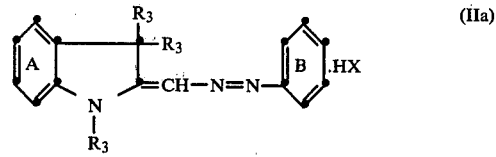

wherein $R_3$, A and B are as defined for formula I and X is any anion, in aqueous alkaline medium having a pH value of at least 10, with at least 2 moles of a compound that introduces the radical R. The carbinol bases obtained are valuable intermediates for obtaining in particular cationic compounds containing any anions, especially carboxylic acid anions, most preferably an acetate anion.

9 Claims, No Drawings

PROCESS FOR THE PRODUCTION OF CARBINOL BASES FROM INDOLINE COMPOUNDS

The present invention relates to a novel process for the production of carbinol bases from indoline compounds and to the use of these bases for obtaining cationic compounds, and to concentrated aqueous liquid formulations of such cationic compounds.

It is known to obtain carbinol bases of the formula Ia

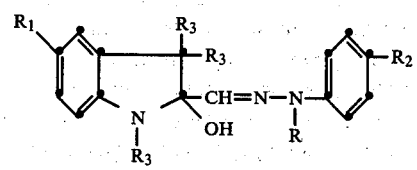

wherein R is the methyl or ethyl group, $R_1$ is hydrogen or halogen, $R_2$ is hydrogen, a $C_1$–$C_4$alkyl radical, a $_1$–$C_4$alkoxy radical, a phenoxy radical, an azobenzene radical or the radical of the formula —O—$(CH_2)_n$—O—$R_4$, wherein n is 1 or 2 and $R_4$ is a $C_1$–$C_4$alkyl radical, the phenyl radical or also the —$CH_2$— radical if n is 1 and this —$CH_2$— group is attached to a 6-membered ring system in the ortho-position to $R_2$, and each $R_3$ independently is a $C_1$–$C_4$alkyl group, by starting from cationic compounds of the formula III

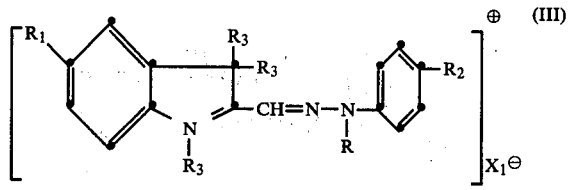

wherein R, $R_1$, $R_2$ and $R_3$ are as defined for formula I and $X_1$ is any anion, and reacting these compounds with a base, e.g. NaOH.

Anions $X_1$ are e.g.: halogen such as chloride, bromide or iodide, sulfate, methylsulfate, aminosulfate, carbonate, bicarbonate, phosphate, phosphomolybdate, phosphotungstate, phosphotungstomolybdate, benzenesulfonate, naphthalenesulfonate, 4-chlorobenzenesulfonate or complex anions.

The cationic compounds of the formula III are obtained e.g. by quaternisation of the corresponding dye bases of the formula IIb

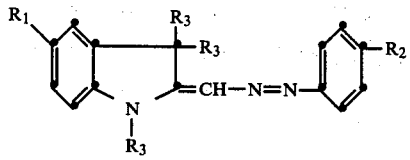

(known e.g. from British patent specification No. 1,544,290 and German Offenlegungsschrift No. 2 620 790) in aqueous medium.

This procedure accordingly requires two steps to obtain the carbinol bases, namely a first step by quaternising the dye base of the formula IIb and a second step by reacting the isolated quaternisation product of the formula III with a base.

The carbinol bases are of key importance to the extent that they constitute starting materials for obtaining cationic compounds containing any anion. In particular, carboxylic acid salts, especially acetates, can only be obtained via the carbinol bases, which has up to now been done by preparing first the halide or methanesulfate by quaternisation, then isolating the quaternisation product of the formula III and subsequently reacting it to give the carbinol base, if desired isolating the carbinol base, from which finally the carboxylic acid salt (e.g. acetate) of the cationic compound can be obtained. This procedure requires altogether three steps.

It is the object of the present invention to provide a simpler and more economic process for obtaining carbinol bases without having to isolate cationic compounds as intermediates.

Accordingly, the present invention provides a single step process for the preparation of carbinol bases of the formula I

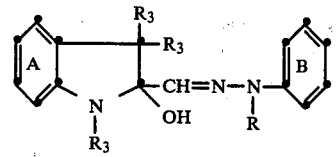

wherein R is the methyl or ethyl group, each $R_3$ independently is a $C_1$–$C_4$alkyl group, and the benzene rings A and/or B can be unsubstituted or substituted, which process comprises alkylating 1 mole of a dye base of the formula II

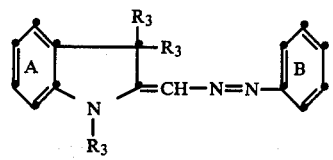

or the hydrogen salt thereof of the formula IIa

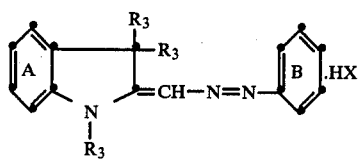

wherein $R_3$, A and B are as defined for formula I and X is any anion, in particular a chloride, sulfate or hydrogen sulfate anion, in aqueous alkaline medium having a pH value of at least 10, with at least 2 moles of a compound that introduces the radical R (alkylating agent).

The alkylation is carried out with diethyl sulfate or, preferably, with dimethyl sulfate, using at least 2 equivalents, preferably 2 to 4 and, most preferably, at least 3, equivalents of dimethyl sulfate or diethyl sulfate, based on the dye base of the formula II or IIa. There is no restriction on the upper limit to the number of equivalents of alkylating agent. It is possible to use e.g. 100 equivalents of alkylating agent, the upper limit being determined alone by considerations of economy. The process is normally carried out in alkaline medium, which is prepared by addition of alkali lye, e.g. NaOH, while keeping the pH before or during the reaction at or above 10, preferably at 11, and in the temperature range from 0° to 60° C., in particular from 20° to 45° C. The carbinol bases of the formula I are obtained by this single step procedure in virtually quantitative yield. The preferred starting materials are dye bases of the formula IIa, wherein X is a chloride, sulfate or, in particular, hydrogen sulfate anion.

The novel process is of particular interest for obtaining carbinol bases of the formula Ia

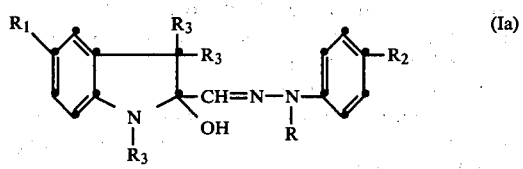

wherein R is the methyl or ethyl group, $R_1$ is a hydrogen or halogen, $R_2$ is hydrogen, a $C_1$-$C_4$alkyl radical, a $C_1$-$C_4$alkoxy radical, a phenoxy radical, an azobenzene radical or a radical of the formula —O—($CH_2$)$_n$—O—$R_4$, wherein n is 1 or 2 and $R_4$ is a $C_1$-$C_4$alkyl radical, the phenyl radical or also the —$CH_2$— radical if n is 1 and this —$CH_2$— group is attached to a 6-membered ring system in the ortho-position to $R_2$, and each $R_3$ independently is a $C_1$-$C_4$alkyl group, which process comprises alkylating a dye base of the formula IIb

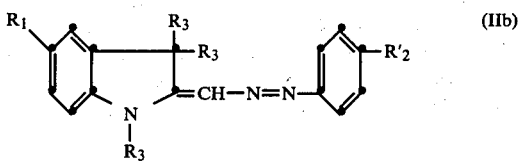

or the hydrogen salt thereof of the formula IIc

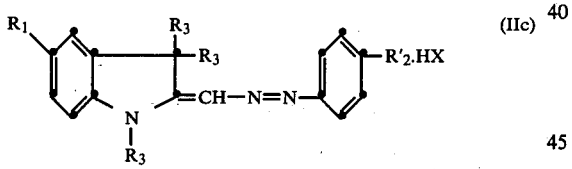

in which formulae $R_1$ and $R_3$ are as defined for formula Ia and $R_2'$ has the meaning of $R_2$ as given for formula Ia or is OH, and in which $R_4$ within the definition of $R_2$ is also hydrogen and X is an anion, preferably a chloride, sulfate or hydrogen sulfate anion, in aqueous alkaline medium having a pH of at least 10, with at least 2 moles, preferably 2 to 4 moles, of a compound that introduces the radical R, preferably dimethyl sulfate.

$R_1$ as a halogen atom is a fluorine, chlorine or bromine atom.

$R_2$ as a $C_1$-$C_4$alkyl group is an unsubstituted, unbranched or branched alkyl group, e.g. the methyl, ethyl or isopropyl group. $R_2$ as a $C_1$-$C_4$alkoxy group is, in particular, the methoxy or ethoxy group; and $R_2$ as the —O—($CH_2$)$_n$—O—$R_4$ group is, in particular, phenoxymethoxy, phenoxyethoxy, (n- and iso)butoxymethoxy, (n- and iso)butoxyethoxy, (n- and iso)propoxymethoxy, (n- and iso)propoxyethoxy, ethoxymethoxy, ethoxyethoxy and methoxyethoxy. When n is 1 then $R_4$ can also be a —$CH_2$— group which is attached to a 6-membered ring in the ortho-position to $R_2$.

Each $R_3$ independently as an alkyl group can be unbranched or branched and is preferably the —$CH_3$— group.

The carbinol bases of the formula I or Ia are insoluble in water and can accordingly be isolated readily from the reaction medium. They are valuable starting materials for obtaining cationic compounds of the formula III by reaction with a compound $HX_2$ wherein $X_2$ is any anion. $HX_2$ is, in particular, a carboxylic acid such as acetic acid, from which the acetates are then obtained.

The great advantage of the process of the invention consists in the fact that e.g. the readily soluble dyestuff acetates, which are most suitable for liquid formulations, can be obtained in simple manner.

Surprisingly, very good volume yields and pure carbinol bases can also be obtained by the process of the invention. The volume yields are substantially better than those obtained by the known processes, in which the cationic compound III is converted into the carbinol bases Ia. Finally, attention must also be drawn to the fact that the carbinol base I or Ia can be presented direct from a non-quaternised dye base II, IIa, IIb or IIc.

The invention is illustrated, but not limited, by the following Examples, in which parts are by weight unless otherwise indicated.

EXAMPLE 1

26.8 parts of the dye base of the formula

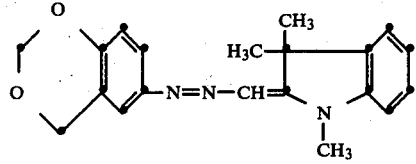

are added at 20°–25° C. to a mixture of 50 parts of water and 30.2 parts (3 moles) of dimethyl sulfate. With efficient stirring, 10.4 parts of 10 N sodium hydroxide solution are added dropwise at 20°–30° C. over 1 hour, such that the pH of the reaction mixture is kept between 11 and 12. The reaction mixture is then warmed to 40°–45°. C. and the pH is kept at 12 for 1 hour by adding further NaOH. The well crystallised carbinol base of the formula

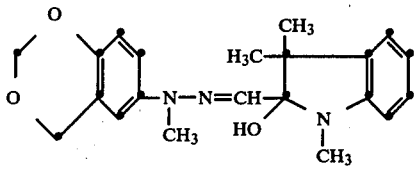

is collected by filtration, washed with 20 parts of water and dried at 40° C. in vacuo, affording 28.5 parts of a pale yellow powder.

EXAMPLE 2

Starting at 20°–25° C., 27.5 parts of the dye base hydrochloride of the formula

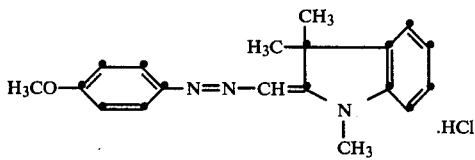

are added to a mixture of 50 parts of water and 40.3 parts (4 moles) of dimethyl sulfate. With efficient stirring, the reaction mixture is then kept at pH 11 by the dropwise addition of 10 N NaOH, in the course of which addition the temperature rises to about 40° C. Crystals of the carbinol base of the formula

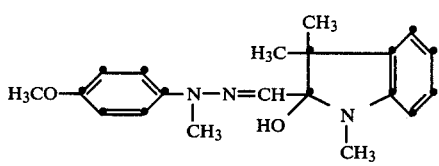

precipitate and are collected by filtration and dried in vacuo at 40° C., affording 26 parts of a yellow powder which is readily soluble in toluene and insoluble in water.

The same product is obtained by starting from the $HSO_4$ salt instead of the HCl salt.

EXAMPLE 3

The moist filter cake of Example 2 (=approx. 34 parts of aqueous carbinol base) is mixed at 20°–25° C. with 31 parts of glacial acetic acid. After a short time a clear, concentrated stable dyestuff solution containing the dye salt of the formula

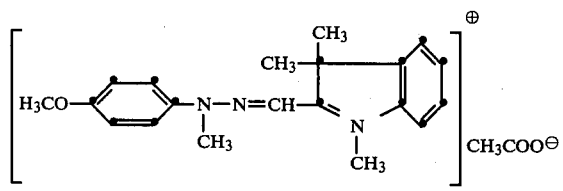

is obtained. Golden-yellow dyeings and prints of excellent fastness properties are obtained therewith on acrylic fibres.

What is claimed is:

1. A process for the production of a carbinol base of the formula

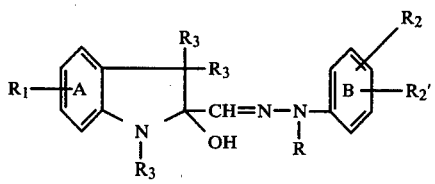

wherein
R is methyl or ethyl,
each $R_3$ independently is a $C_1$–$C_4$alkyl group,
$R_1$ is hydrogen or halogen,
$R_2$ is hydrogen, a $C_1$–$C_4$alkyl radical, a $C_1$–$C_4$alkoxy radical, a phenoxy radical, an azobenzene radical or a radical of the formula $-O-(CH_2)_n-OR_4$, wherein n is 1 or 2 and $R_4$ is a $C_1$–$C_4$alkyl radical, a phenyl radical, or, when n is 1, $R_2$ and $R_2'$ are ortho to each other and together form a fused ring of formula $-O-CH_2-OCH_2-$, and otherwise $R_2'$ is hydrogen which process comprises alkylating 1 mole of a dye base of the formula

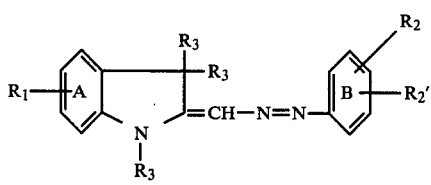

or an acid (HX) salt thereof
wherein X is any anion, in aqueous alkaline medium having a pH value of at least 10, with at least 2 moles of a compound that introduces the radical R.

2. A process of claim 1, wherein $R_1$ and $R_2$ are both para to the nitrogen substituents on their respective rings.

3. A process of claim 2, wherein X is a chloride, sulfate or hydrogen sulfate anion.

4. A process of claim 2, wherein the compound employed to introduce the radical R is dimethyl sulfate or diethyl sulfate.

5. A process of claim 4, wherein at least 3 moles of dimethyl sulfate or diethyl sulfate are used.

6. A process of claim 4, wherein 2 to 4 moles of dimethyl sulfate are used.

7. A process of claim 2, wherein the pH of the reaction medium is 11 or higher than 11.

8. A process of claim 2, wherein the alkylation is carried out in the temperature range from 0° to 60° C.

9. A process of claim 8, wherein the alkylation is carried out in the temperature range from 20°–45° C.

* * * * *